United States Patent [19]

Goto et al.

[11] Patent Number: 5,250,216
[45] Date of Patent: Oct. 5, 1993

[54] 1-(4-ALKYLPHENYLETHYNYL)-4-(ALKYL-PHENYLETHYNYL)-BENZENE

[75] Inventors: Yasuyuki Goto; Kisei Kitano, both of Chiba, Japan

[73] Assignee: Chisso Corporation, Ohsaka, Japan

[21] Appl. No.: 711,276

[22] Filed: Jun. 4, 1991

Related U.S. Application Data

[63] Continuation of Ser. No. 356,928, May 25, 1989, abandoned.

[30] Foreign Application Priority Data

May 31, 1988 [JP] Japan ................. 63-133577

[51] Int. Cl.$^5$ ............... C09K 19/06; C07C 15/12
[52] U.S. Cl. .................... 252/299.6; 585/25
[58] Field of Search ......... 585/25; 252/299.5, 299.6, 252/299.01

[56] References Cited

U.S. PATENT DOCUMENTS

| | | | |
|---|---|---|---|
| 3,925,482 | 12/1975 | Jacques | 252/299.6 |
| 4,528,114 | 7/1985 | Petrzilka | 252/299.6 |
| 4,726,910 | 2/1988 | Takatsu et al. | 252/299.5 |
| 4,778,620 | 10/1988 | Goto et al. | 252/299.5 |
| 4,816,180 | 3/1989 | Goto et al. | 252/299.63 |
| 4,874,543 | 10/1989 | Yoshida | 252/299.61 |
| 4,895,672 | 1/1990 | Goto et al. | 252/299.63 |

FOREIGN PATENT DOCUMENTS

| | | | |
|---|---|---|---|
| 345013 | 12/1989 | European Pat. Off. | 585/25 |
| 2083340 | 3/1990 | Japan | 585/25 |

OTHER PUBLICATIONS

Chemical Abstracts 90(25):203162K, Photophysical Properties of Molecules Containing Triple Bonds, 1979.
Adomenas, P. et al., Advances in Liquid Crystal Research and Applications, vol. 2, 1981, pp. 1029–1038.
Stanley Wentworth, Polymer Preprints, vol. 15, No. 1, pp. 697–700, (1974).

*Primary Examiner*—Philip Tucker
*Attorney, Agent, or Firm*—Wenderoth, Lind & Ponack

[57] ABSTRACT

A tolan derivative useful as a component of liquid crystal materials and being superior to conventional tolan derivatives in the characteristics of Δn and viscosity, and a liquid crystal composition containing the same are provided, which tolan derivative is expressed by the formula

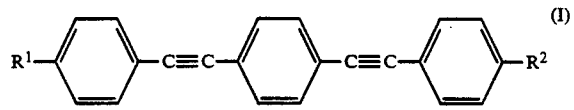

wherein $R^1$ and $R^2$ each represent an alkyl group of 1 to 10 carbon atoms.

2 Claims, 2 Drawing Sheets

1-(4-ALKYLPHENYLETHYNYL)-4-(ALKYL-PHENYLETHYNYL)-BENZENE

This application is a continuation of now abandoned application, Ser. No. 07/356,928 filed May 25, 1989.

BACKGROUND OF THE INVENTION

1. Field of the Invention

This invention relates to a 1-4-(alkylphenyl-ethynyl)-4-(alkylphenylethynyl)benzene as a substituted benzene derivative used as a component of liquid crystal materials and a liquid crystal composition containing the derivative.

2. Description of the Related Art

Display devices having applied liquid crystals utilize an electrooptical effect based on the anisotropies of the dielectric constant and electric conductivity of liquid crystal substances. Liquid crystal display modes include various ones such as dynamic scattering mode, twisted nematic mode, super-twist nematic mode, phase transition mode, DAP mode, guest-host mode, etc. Properties required for liquid crystal substances used for liquid crystal display vary depending on the respective liquid crystal display modes, but a broad mesomorphic range, good stabilities to moisture, air, light, electricity, etc. and the like are required in common to any of the display modes. Further, it is also required that when display elements are used in the liquid crystal display devices, the response of the display elements is quick and the devices can be driven at a voltage as low as possible. At present, however, there is no single compound satisfying all of these requirements; hence, practically, liquid crystal compositions obtained by blending several kinds of liquid crystal compounds or these compounds with compounds similar to liquid crystals have been used.

Recently, in order to provide a liquid crystal display element having a good image quality even in a multiplex number of 100 or more, it has been proposed to change the cell structure wherein the twist angle of the helical structure of liquid crystal molecule is combined with a polarizing plate, into a novel mode (e.g. Japanese patent application laid-open No. Sho 60-50511 (1985), etc.).

The case of a liquid crystal display element of a cell structure having an increased the twist angle of the liquid crystal molecule exhibits an entirely different tendency from that of the case of conventional 90° twist, in the effect on physical properties obtained by choosing liquid crystal materials.

FIGS. 1a and 1b illustrate the characteristics of a liquid crystal display element having an increased twist angle of a liquid crystal molecule as compared with those of conventional 90° twist, in terms of the angle of view and the angle dependency of voltage-transmittance characteristics. FIGS. 1a and 1b illustrate a case of 90° twist and a case of 180° twist, respectively. As seen from FIGS. 1a and 1b, the element having a structure of 180° twist is steep in the rise characteristic (Y characteristic) of transmittance depending on voltage, and this characteristic is evidently improved as compared with the case of conventional 90° twist. This tendency becomes more notable with increase of twist angle. As described above, since the element having an element structure increased in the twist angle is steep in the rise characteristic brought about by voltage, the transmittance difference between voltage impression and nonimpression at the time of multiplex drive increases so that a multiplex drive higher than a conventional one becomes possible.

However, as to the relationship between the γ characteristic in the case of 90° twist and that in the case of about 200° twist, the same tendency is not exhibited depending upon liquid crystal materials; thus there has come to appear a tendency which does not apply to the general report that, in the case of 90° twist, materials having a good γ characteristic are superior when the ratio of elastic constants ($K_{33}/K_{11}$) is low (Gunter Baur, Euro Display, 84 "Liquid crystal properties in relation to multiplexing requirements"). This is presumed to be related to the elastic constant of twist and other factors, but it has not yet been elucidated. FIG. 2 shows a relationship between the ratio of elastic constants and the γ characteristic in the cases of 180° twist and 230° twist as to two kinds of compounds, i.e. pyrimidines and PCHs (phenylcyclohexanes). As seen from FIG. 2, pyrimidines having smaller elastic constants are inferior to PCHs in the γ characteristic. In FIG. 2, γ 10°, 80–20% refers to a γ characteristic in terms of the ratio of a voltage at 80% transmittance to that at 20% transmittance in the case of an angle of 10° against normal. As described above, in the case of about 200° twist, a conventional way of thinking does not apply, and it is necessary to choose liquid crystal materials on a different basis from that in the case of the cell structure of 90° twist. As described above, by increasing the twist angle or researching liquid crystal materials, a liquid crystal display element having a good γ characteristic is obtained. However, a new phenomenon has been clarified by improving the γ characteristic the γ characteristic of liquid crystal materials, the lower the response rate, as shown in FIG. 3. When the response properties are taken into consideration, choice a of only a material having a good γ characteristic is not sufficient, but in order to obtain a liquid crystal display element having good response properties, while maintaining γ characteristic to a certain extent, a method of reducing the thickness of the liquid crystal layer is proposed.

Thus, with accompaniment of reducing the thickness of the liquid crystal layer in order to improve the response properties, the optical anisotropy value Δn of the material should be varied. In the case of 200° C. twist, the product of the Δn of the liquid crystal material by the thickness d of the liquid crystal layer (Δn×d) is best in the vicinity of 0.96 μm. When the thickness d of the liquid crystal layer is 7 μm, the Δn of the material should be adjusted to 0.137. In order to make the thickness of the liquid crystal layer 5 μm for improving the response rate, it is necessary to increase the Δn to 0.192. As described above, in order to correspond to thinning of the liquid crystal layer, the Δn of the material should be increased, but in this case, there is a problem of viscosity. As to the relationship between the Δn and viscosity of liquid crystal materials so far reported, a tendency that the viscosity increases with increase in the Δn has been clarified. Namely, conventional materials having a large Δn and yet a low viscosity have been very few.

As examples of so far known compounds having a large optical anisotropy value Δn when used as a component of liquid crystal materials, compounds expressed by the following formulas (1)–(4) are disclosed in (1) French patent application laid-open No. 2,141,438, (2) Japanese patent application laid-open No. Sho 60-152427/1985, (3) Japanese patent application laid-open No. Sho 61-260031/1986 and (4) Japanese patent application laid-open No. Sho 60-204731/1985, respectively:

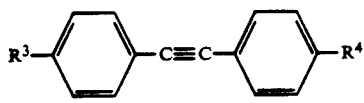
(1)

wherein $R^3$ and $R^4$ each represent an alkyl group or an alkoxy group;

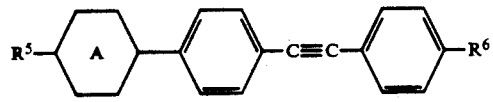
(2)

and $R^5$ and $R^6$ each represent a linear alkyl group;

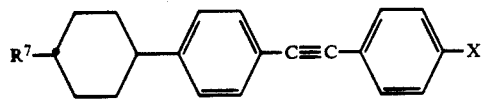
(3)

wherein $R^7$ represents a linear alkyl group and X represents a halogen atom; and

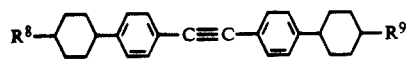
(4)

wherein $R^8$ and $R^9$ each represent a linear alkyl group.

These tolan derivatives have been said to have a large $\Delta n$ and a relatively low viscosity, but compounds far exceeding the characteristics of these compounds have recently been required.

SUMMARY OF THE INVENTION

The present invention resides in a 1-(4-alkylphenylethynyl)-4-(alkylphenylethynyl)-benzene expressed by the formula

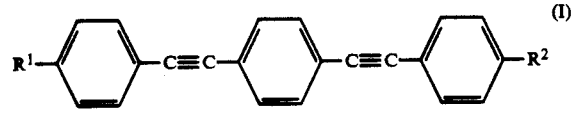
(I)

wherein $R^1$ and $R^2$ each represent an alkyl group of 1 to 10 carbon atoms, and a liquid crystal mixture containing the same.

DETAILED DESCRIPTION OF PREFERRED EMBODIMENTS

Figure 1A:
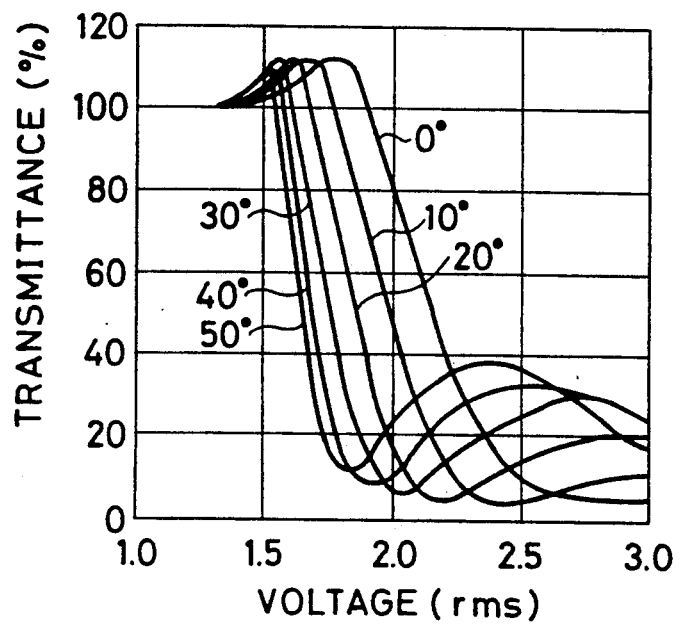
FIG. 1a shows a chart illustrating the angle dependency of the voltage transmittance characteristic of an element having a twist angle of 90°.
Figure 1B:
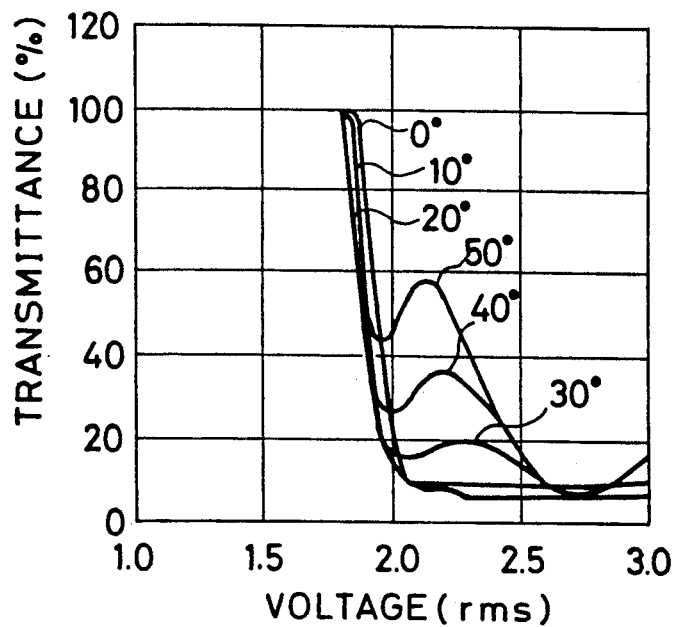
FIG. 1b shows a chart illustrating the angle dependency of the voltage-transmittance characteristic of an element having a twist angle of 180°.
Figure 2:
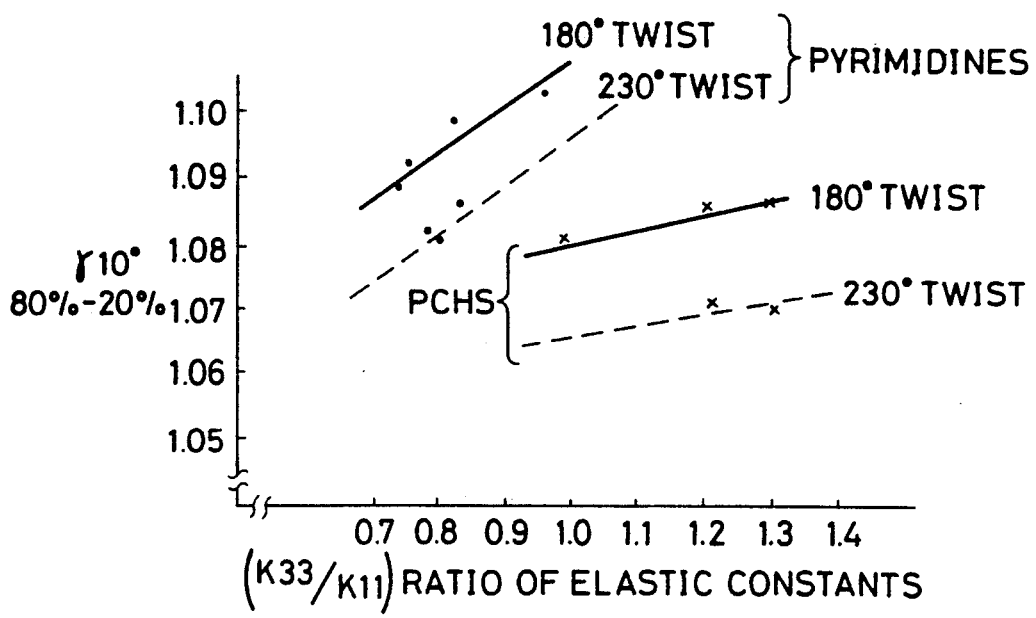
FIG. 2 shows a chart illustrating the relationship between the ratio of the elastic constant of an element of twist angle 180° to that of twist angle 230° and, $\gamma$-characteristic.
Figure 3:
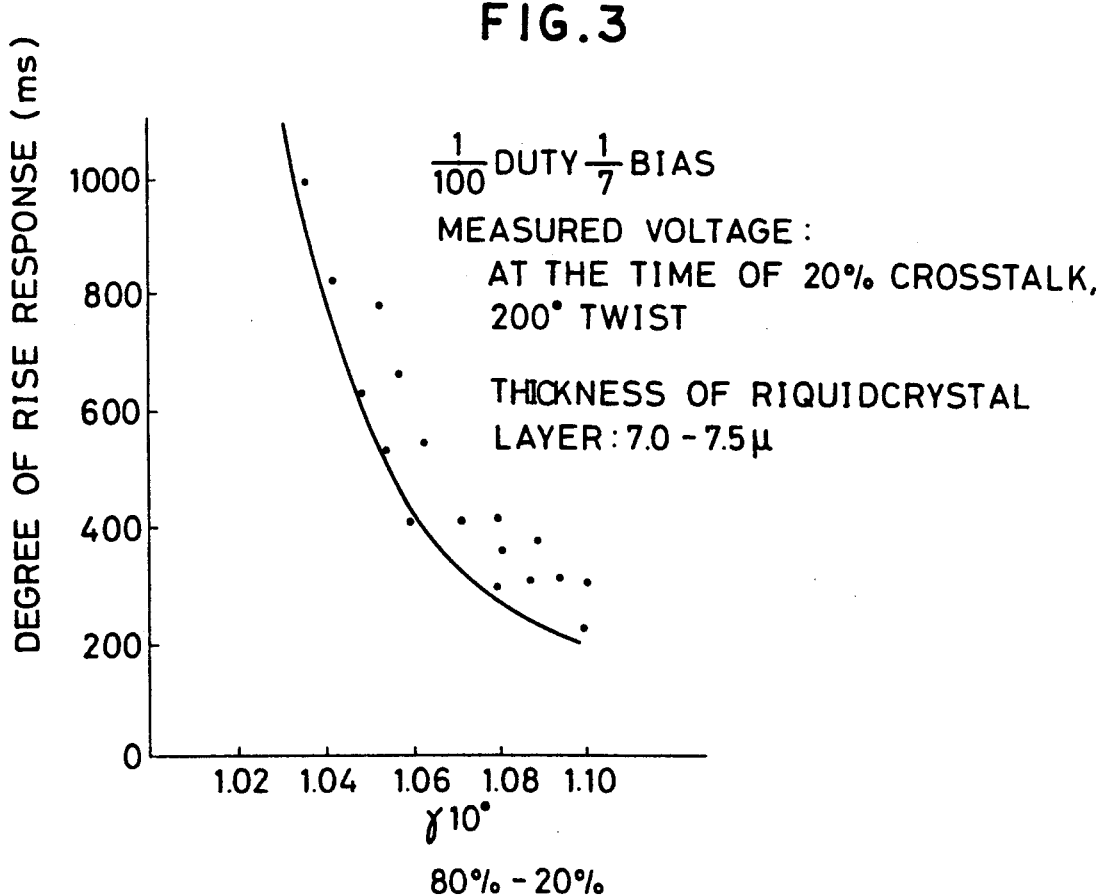
FIG. 3 shows a chart illustrating the relationship between the $\gamma$-characteristic and the rise response rate of a conventional liquid crystal material.

Examples of the compound provided by the present invention are as follows:

1,4-bis-(4-methylphenylethynyl)benzene,
1,4-bis-(4-ethylphenylethynyl)benzene,
1,4-bis-(4-propylphenylethynyl)benzene,
1,4-bis-(4-butylphenylethynyl)benzene,
1,4-bis-(4-pentylphenylethynyl)benzene,
1,4-bis-(4-hexylphenylethynyl)benzene,
1,4-bis-(4-heptylphenylethynyl)benzene,
1,4-bis-(4-octylphenylethynyl)benzene,
1,4-bis-(4-nonylphenylethynyl)benzene,
1,4-bis-(4-decylphenylethynyl)benzene,
1-(4-methylphenylethynyl)-4-(4-ethylphenylethynyl)-benzene,
1-(4-methylphenylethynyl)-4-(4-propylphenylethynyl)-benzene,
1-(4-methylphenylethynyl)-4-(4-butylphenylethynyl)-benzene,
1-(4-methylphenylethynyl)-4-(4-pentylphenylethynyl)-benzene,
1-(4-methylphenylethynyl)-4-(4-hexylphenylethynyl)-benzene
1-(4-methylphenylethynyl)-4-(4-heptylphenylethynyl)-benzene,
1-(4-methylphenylethynyl)-4-(4-octylphenylethynyl)-benzene,
1-(4-methylphenylethynyl)-4-(4-nonylphenylethynyl)-benzene,
1-(4-methylphenylethynyl)-4-(4-decylphenylethynyl)-benzene,
1-(4-ethylphenylethynyl)-4-(4-propylphenylethynyl)-benzene,
1-(4-ethylphenylethynyl)-4-(4-butylphenylethynyl)benzene,
1-(4-ethylphenylethynyl)-4-(4-pentylphenylethynyl)-benzene,
1-(4-ethylphenylethynyl)-4-(4-hexylphenylethynyl)benzene,
1-(4-ethylphenylethynyl)-4-(4-heptylphenylethynyl)-benzene,
1-(4-ethylphenylethynyl)-4-(4-octylphenylethynyl)benzene,
1-(4-ethylphenylethynyl)-4-(4-nonylphenylethynyl)-benzene,
1-(4-ethylphenylethynyl)-4-(4-decylphenylethynyl)benzene,
1-(4-propylphenylethynyl)-4-(4-butylphenylethynyl)-benzene,
1-(4-propylphenylethynyl)-4-(4-pentylphenylethynyl)-benzene,
1-(4-propylphenylethynyl)-4-(4-hexylphenylethynyl)-benzene,
1-(4-propylphenylethynyl)-4-(4-heptylphenylethynyl)-benzene,
1-(4-propylphenylethynyl)-4-(4-octylphenylethynyl)-benzene
1-(4-propylphenylethynyl)-4-(4-nonylphenylethynyl)-benzene, 1-(4-propylphenylethynyl)-4-(4-decylphenylethynyl)-benzene,
1-(4-butylphenylethynyl)-4-(4-pentylphenylethynyl)-benzene,
1-(4-butylphenylethynyl)-4-(4-hexylphenylethynyl)benzene,
1-(4-butylphenylethynyl)-4-(4-heptylphenylethynyl)-benzene,
1-(4-butylphenylethynyl)-4-(4-octylphenylethynyl)benzene,
1-(4-butylphenylethynyl)-4-(4-nonylphenylethynyl)-benzene,
1-(4-butylphenylethynyl)-4-(4-decylphenylethynyl)benzene,
1-(4-pentylphenylethynyl)-4-(4-hexylphenylethynyl)-benzene,
1-(4-pentylphenylethynyl)-4-(4-heptylphenylethynyl)-benzene,
1-(4-pentylphenylethynyl)-4-(4-octylphenylethynyl)-benzene,
1-(4-pentylphenylethynyl)-4-(4-nonylphenylethynyl)-benzene,
1-(4-pentylphenylethynyl)-4-(4-decylphenylethynyl)-benzene,
1-(4-hexylphenylethynyl)-4-(4-heptylphenylethynyl)-benzene,
1-(4-hexylphenylethynyl)-4-(4-octylphenylethynyl)benzene,
1-(4-hexylphenylethynyl)-4-(4-nonylphenylethynyl)-benzene,
1-(4-hexylphenylethynyl)-4-(4-decylphenylethynyl)-benzene,
1-(4-heptylphenylethynyl)-4-(4-octylphenylethynyl)-benzene,
1-(4-heptylphenylethynyl)-4-(4-nonylphenylethynyl)-benzene,
1-(4-heptylphenylethynyl)-4-(4-decylphenylethynyl)-benzene,
1-(4-octylphenylethynyl)-4-(4-nonylphenyl-ethynyl)-benzene,
1-(4-octylphenylethynyl)-4-(4-decylphenyl-ethynyl)-benzene and
1-(4-nonylphenylethynyl)-4-(4-decylphenyl-ethynyl)-benzene.

The compound provided by the present invention has specific features desired as liquid crystal component a in well-balanced manner; namely the compound has an optical anisotropy $\Delta n$ as very large as about 0.4, a viscosity at 20° C. of about 20 cp which is low for a compound of three-ring structure, a high clearing point, etc.

PREPARATION OF COMPOUND

Next, an embodiment of preparation of the compound of the present invention will be illustrated.

A symmetric compound may be prepared according to the following equation:

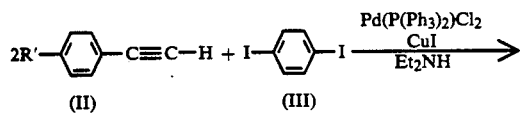

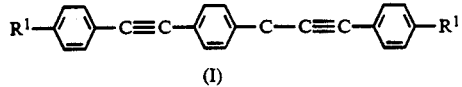

Namely, when an alkylphenylacetylene (II) is reacted with 1,4-diiodobenzene (III) in a solvent of diethylamine in the presence of Pd catalyst and copper iodide according to a method in the literature (TetraL hedron Letters No. 50, pp. 4467–4470, 1975), it is possible to prepare the objective compound (I).

Further, an asymmetric compound may be prepared according to the following equation:

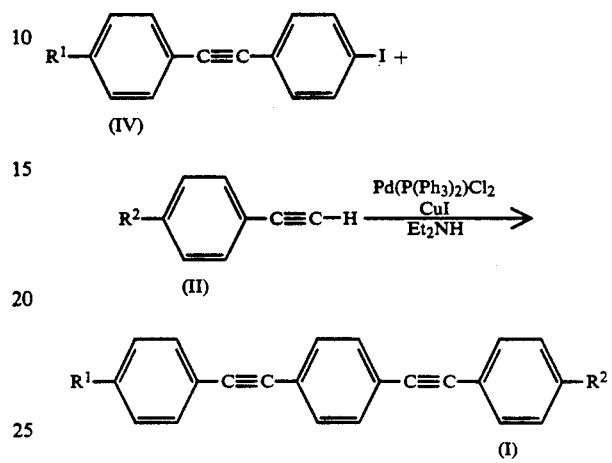

Namely, when a 4-alkylphenylacetylene (II) is reacted with a 4-alkyl-4'-iodotolan (IV) which can be prepared in a conventional manner, according to the above-mentioned method, it is possible to obtain the objective asymmetric compound (I) ($R^1$ and $R^2$ in the above equation being as defined above).

The liquid crystal composition comprises at least two kinds of liquid crystals or compounds similar to liquid crystals and at least one of them is a liquid crystal compound expressed by the above formula (I), the content of which is preferably in the range of 2 to 30% by weight.

Further, the liquid crystal composition containing the above liquid crystal compound (I) is preferably used in a liquid crystal element wherein a nematic liquid crystal having an optically active substance added thereto and having a positive dielectric anisotropy is filled between a pair of opposed upper and lower electrode substrates; the liquid crystal molecule forms a helical structure of 160°–270° twist in the direction of its thickness; the polarizing axis of polarizing plates provided so as to place the helical structure therebetween is deviated in the range of 20°–70° against the aligning direction of liquid crystal molecules between the electrode substrates; and the product of the thickness d of the liquid crystal layer by the dielectric anisotropy $\Delta n$ of the liquid crystal layer, $\Delta n \times d$, is 0.7–1.2 μm.

As to a component of the liquid crystal composition of the present invention, and as compounds used in admixture with the compound of the formula (I), the following compound groups (i)–(xxxiii) are enumerated:

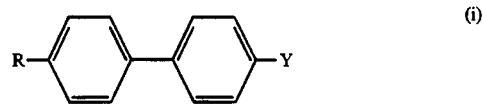

-continued
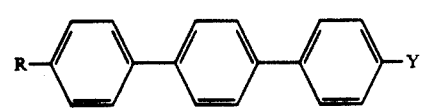 (ii)
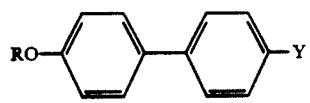 (iii)
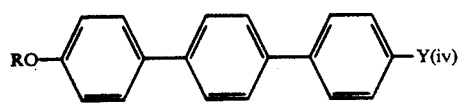 (iv)
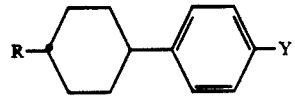 (v)
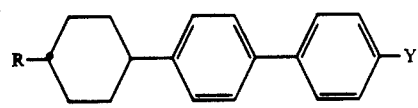 (vi)
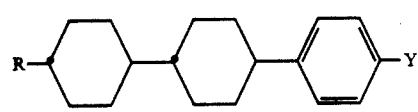 (vii)
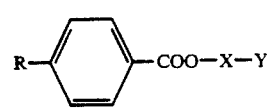 (viii)
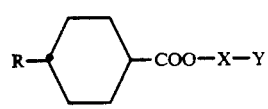 (ix)
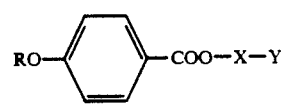 (x)
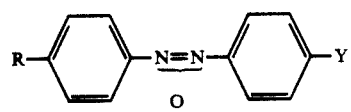 (xi)
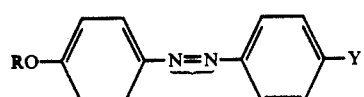 (xii)
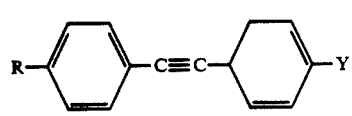 (xiii)
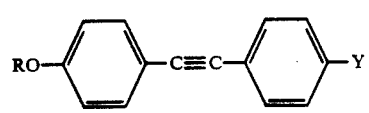 (xiv)
-continued
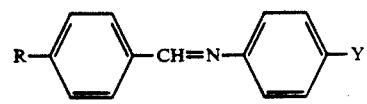 (xv)
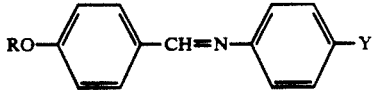 (xvi)
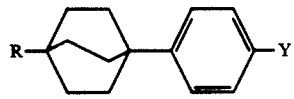 (xvii)
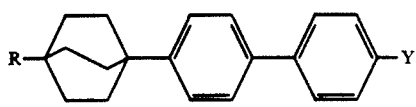 (xviii)
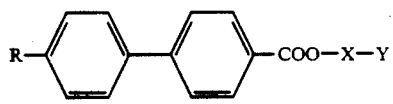 (xix)
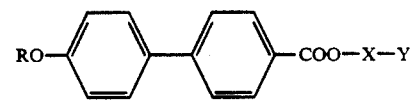 (xx)
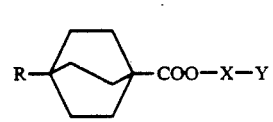 (xxi)
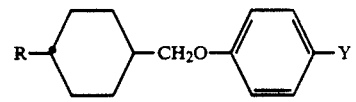 (xxii)
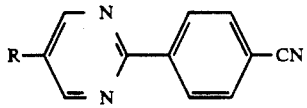 (xxiii)
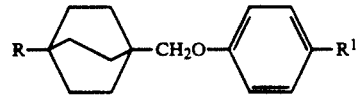 (xxiv)
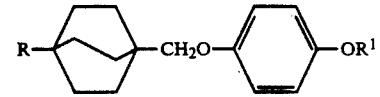 (xxv)
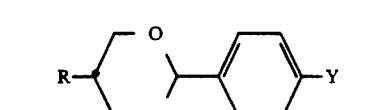 (xxvi)
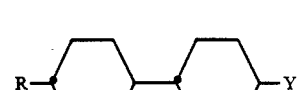 (xxvii)

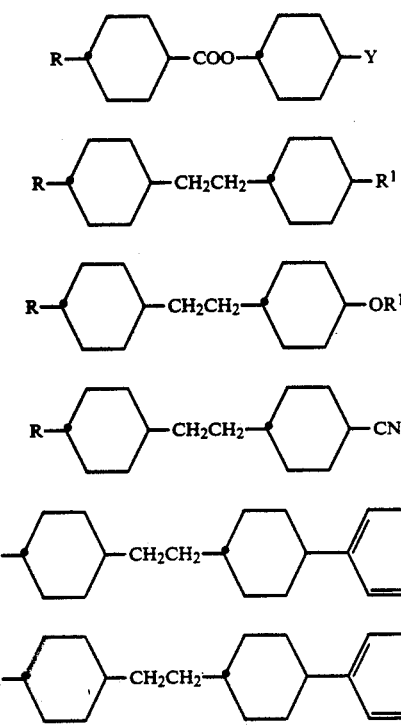

(xxviii)
(xxix)
(xxx)
(xxxi)
(xxxii)
(xxxiii)

In the formulas (i)-(xxxiii), X represents

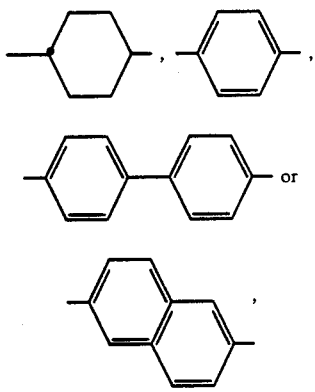

γ represents —CN, halogen atom, $R^1$ or —$OR^1$ and R and $R^1$ each represent an alkyl group.

The present invention will be described in more detail by way of Examples, but it should not be construed to be limited thereto.

In the Examples, C-N point represents liquid crystal-nematic phase transition point and N-I point represents nematic phase-isotropic liquid phase transition point.

EXAMPLE 1

Preparation of 1,4-bis-(4-propylphenylethynyl)-benzene 1,4-Diiodobenzene (2.5 g, 7.57 mmol) was added to diethylamine (80 ml) in nitrogen gas stream, followed by agitating the mixture at room temperature, successively adding copper iodide (60 mg) and dichlorobis(triphenylphosphine)palladium(II) (100 mg), adding 4-propylphenylacetylene (4.37 g, 30 mmol) in several steps, agitating the reaction mixture at room temperature overnight, adding water (200 ml), extracting the resulting deposited crystals with toluene (100 ml), washing the toluene solution with dilute hydrochloric acid, water, an aqueous solution of sodium hydrogen sulfate and water in this order, drying the solution on anhydrous sodium sulfate, passing it through a short column of activated alumina, distilling off toluene and recrystallizing the residue from ethyl acetate to obtain the objective 1,4-bis-(4-propylphenyl-ethynyl)benzene (1.92 g, 5.3 mmol). This product exhibited liquid crystal phases. C-N point: 179.1° C. N-I point: 245.5° C.

EXAMPLE 2, 3 and 4

The following compounds were obtained in the same manner as in Example 1:
1,4-bis-(4-ethylphenylethynyl)benzene
(C-N point: 208.9° C., N-I point: 235.8° C.).
1,4-bis-(4-butylphenylethynyl)benzene
(C-N point: 151.8° C., N-I point: 215.9° C.).
1,4-bis-(4-pentylphenylethynyl)benzene
(C-N point: 151.1° C., N-I point: 212.3° C.).

USE EXAMPLE 1

A liquid crystal composition A consisting of
trans-4-propyl-(4-cyanophenyl)cyclohexane
    30 parts by weight,
trans-4-pentyl-(4-cyanophenyl)cyclohexane
    40 parts by weight And
trans-4-heptyl-(4-cyanophenyl)cyclohexane
    30 parts by weight,
had a N-I point of 52.1° C., a dielectric anisotropy Δε of 10.7, a viscosity at 20° C. of 22.4 cp and an optical anisotropy Δn of 0.118. When 1,4-bis-(4-butylphenylethynyl)-benzene of the present invention shown in Example 3 (5 parts by weight) was added to the above liquid crystal composition A (95 parts by weight), the resulting liquid crystal composition exhibited a N-I point raised up to 57.2° C., a viscosity at 20° C. of 22.5 cp (unchanged) and an optical anisotropy Δn raised up to 0.131.

USE EXAMPLE 2

To the liquid crystal composition A used in Use example 1 (90 parts by weight) were added 1,4-bis-(4-propylphenylethynyl)benzene (2 parts by weight), [,4-bis-(4-butylphenylethynyl)benzene (5 parts by weight) and 1,4-bis-(4-pentylphenylethynyl)benzene (2 parts by weight), shown in Examples 1, 3 and 4, respectively. The resulting liquid crystal composition exhibited a N-I point of 63.1° C., a viscosity at 20° C. of 22.6 cp and an optical anisotropy Δn of 0.151.

Thus, the usefulness of the compound of the present invention is evident from these examples.

What we claim is:

1. A 1-(4-alkylphenylethynyl)-4-(alkylphenylethynyl)-benzene expressed by the formula

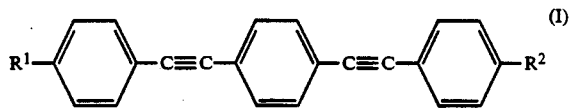

(I)

wherein each of $R^1$ and $R^2$ represents a straight chain alkyl group of 2 to 10 carbon atoms.

2. A liquid crystal composition comprising at least two components at least one of which is a 1-(4-alkylphenylethynyl)-4-(alkylphenylethynyl)-benzene as set forth in claim 1, the content of which is in the range of 2 to 30% by weight based on the weight of said liquid crystal composition.

* * * * *